United States Patent
Goldstein et al.

[11] Patent Number: 5,830,154
[45] Date of Patent: Nov. 3, 1998

[54] DEVICE FOR COLLECTING SUBSTANCES FOR TESTING

[75] Inventors: Andrew Sherman Goldstein, Portland; Charles Edward Bergeron, Lake Oswego; Douglas Logan, Hillsboro, all of Oreg.; Edward Anthony Bezek, Moon Township; Sharon L. Livingood, MacDonald, both of Pa.

[73] Assignee: Epitope, Inc., Beaverton, Oreg.

[21] Appl. No.: 699,102

[22] Filed: Aug. 16, 1996

Related U.S. Application Data

[63] Continuation-in-part of Ser. No. 584,647, Jan. 11, 1996, abandoned.

[51] Int. Cl.⁶ .................................................. A61B 5/00
[52] U.S. Cl. ........................................ 600/572; 600/573
[58] Field of Search ................................ 128/757–758, 128/759, 760; 600/572, 573

[56] References Cited

U.S. PATENT DOCUMENTS

| | | | |
|---|---|---|---|
| 4,175,008 | 11/1979 | White ........................................ | 128/759 |
| 5,022,409 | 6/1991 | Goldstein et al. ....................... | 128/760 |
| 5,103,836 | 4/1992 | Goldstein et al. ....................... | 128/760 |
| 5,234,001 | 8/1993 | Goldstein et al. ....................... | 128/760 |
| 5,339,829 | 8/1994 | Thieme et al. .......................... | 128/760 |
| 5,477,863 | 12/1995 | Grant ....................................... | 128/759 |

FOREIGN PATENT DOCUMENTS 2189883    11/1987    United Kingdom .

*Primary Examiner*—Max Hindenburg
*Attorney, Agent, or Firm*—Townsend and Townsend and Crew

[57] ABSTRACT

A device for collecting substances for testing comprises a vial having a first, generally open end, engageable by a removable closure member, and a second, generally closed end. A removable closure member is provided having first and second ends. The first and second ends of the closure member are engageable with the first end of the vial. An absorbent member is preferably attached to the removable closure member and is receivable in the vial whereby the absorbent member is located outside of the vial prior to use, with the first end of the vial being secured to the second end of the closure member to provide a handle, and after use, the second end of the closure member is removed from the first end of the vial, the closure member is inverted, the absorbent member is inserted into the vial and the first end of the closure member is removably engaged to the first end of the vial.

24 Claims, 5 Drawing Sheets

DEVICE FOR COLLECTING SUBSTANCES FOR TESTING

This application is a Continuation-in-Part of application Ser. No. 08/584,647 filed Jan. 11, 1996, now abandoned.

FIELD OF THE INVENTION

The present invention relates to a device for collecting substances to be tested, and more particularly, to a self-contained device for collecting and preserving substances from the oral cavity of a patient.

BACKGROUND OF THE INVENTION

Many devices are known in the medical field for collecting and preserving substances or specimens for testing. Generally, specimens are collected in a doctor's office or hospital, which does not have the specialized equipment needed for immediate analysis of the collected samples. Testing of certain substances, such as immunoglobulins, is often carried out by testing oral fluids such as saliva because of the association between immunoglobulins and such fluids, as well as the occurrence of sIgA which is peculiar to such fluids. Other testing, such as antigen-antibody testing is also carried out on saliva fluid.

Collection of saliva from the salivary glands is complicated by the low volume secreted, the diverse anatomic dispersion of the glands, and the relatively high viscosity of the fluid. Most techniques for collection involve the use of capillary tubes, suction into micropipette, chewing on paraffin or aspiration into polypropylene syringes. These methods, however, are limited in that the viscosity of the saliva makes the recovery of bubble-free material by these techniques difficult.

Other methods of collection have been suggested to eliminate or at least reduce the quantity of bubbles in the sample. Among such methods include collecting saliva or other fluids in the mouth by direct absorption with a sponge or flexible wad of osmotic membrane. After absorption, the collected fluids can be separated from the absorptive material by centrifugation or by compressing the absorptive material.

Another method for collecting such fluids utilizes a pad which is treated with a hypertonic solution. The use of a hypertonic solution results in a constant production of immunoglobulins from other sources within the oral cavity, those sources not being completely understood. By using a hypertonic solution, it is possible to gain an increase as much as 8 to 16 times more immunoglobulin than by using other mediums, such as distilled water.

A kit has been sold for the collection of sample. The kit includes a first blister pack containing a vial with a break away tip on one end and a removable cap on the other end. Enclosed in the vial between the break away end and the removable cap is preservative.

Interior of the first blister pack, is a second blister pack containing a pad on a semi-rigid tubular stick. Once the first blister pack is opened, the second blister pack is exposed. When this second blister pack is opened, the stick and pad can be removed for the collection of sample.

The specimen is collected on the pad which is attached to the stick-shaped pad holder, designed for easier insertion of the pad into the oral cavity of a patient. Once the fluid sample has been collected, the user must hold the sample on the stick, pick up the vial, and take the cap off the vial. Once the cap is off the vial, using the stick, the pad is inserted into the vial plunging the pad into the preservative solution. In the normal case, most of the length of the stick is broken off at a previously placed score on the stick and the remaining stick and pad sealed by the cap within the vial. The preservative in the vial combines with the pad and collected sample to inhibit microbial growth and enzymatic activity which can destroy antibody molecules, and the closed vial is shipped to a lab.

Once at the lab, the vial is held upside down and the bottom tip is broken off the vial exposing a small opening in the end of the vial. A centrifuge tube is then inverted and placed over the vial. The vial is thus seated in the centrifuge tube, which is then turned right side up. The centrifuge tube with the vial and its broken off tip is then placed in a centrifuge to gravitationally transfer liquid from the pad to the centrifuge tube. The vial with the pad and stick must then be removed from the tube, and the liquid in the tube is then analyzed.

None of the prior art devices provide a collection device for collecting a substance and preserving the substance prior to testing in a self-contained kit form, which is both simple and convenient to use. The known prior art devices include many pieces which must be set down during use which could result in contamination. Additionally, the lab personnel may have to handle the substance capturing media, such as the absorbent pad, for disposal. The present invention is a result of observation of the problems and limitations with the known prior art devices and efforts to solve them.

SUMMARY OF THE INVENTION

Briefly stated, the present invention is a device for collecting substances for testing, such as oral mucosal transudate (OMT) from a location in the mouth between the cheek and gum. The collection device comprises a vial which is ultimately used as the centrifuge tube, having an open end, engageable by a removable closure member, and a second closed end. A removable closure member is provided having first and second closure ends which are each engageable to seal the open end of the vial. An absorbent member is attached to the removable closure member at the first closure end. The absorbent member when attached to the vial by the removable closure but protruding away from the interior of the vial prior to use enables the vial to be used as a handle during sample collection. After use, the second end of the closure member is removed from the vial, the closure member is inverted, and the absorbent member is inserted into the vial. Mixing of the absorbent member with preservative located in the vial, occurs. The sealed vial, and saturated absorbent member can then be shipped to a lab.

At the lab, the sealed vial is then centrifuged. During centrifugation, the preserved sample is separated from the pad. The pad and closure member are then removed and discarded, and the separated preserved sample is analyzed.

It will be understood that the absorbent pad is rectilinear; the pad has a thickness to permit significant absorption, is longer than it is wide, and has a width which forms a close fit to the profile of the vial when the pad is within the vial. The absorbent pad is rounded at the corners for minimum irritation during sample collection with the gum and cheek.

It is important that the pad be secured to the closure member, preferably remaining on the closure during centrifugation. Accordingly, the closure member includes a long semi-rigid pad holding member. This long semi-rigid pad holding member is attached to the closure member the first end, has a bend from its mounting to the closure member that disposes the elongate sides of the pad immediately adjacent to the sides of the vial. The semi-rigid pad holding member defines a U-shaped channel opening to the side of the semi-rigid pad holding member. The semi-rigid pad holding member is rounded at the distal end and ends its U-shaped channel at a seat. The seat is separated from the rounded distal end of the semi-rigid member by a distance to accommodate one elongate side of the rectilinear absorbent pad. A portion of the absorbent pad protrudes beyond the distal end of the semi-rigid pad holding member when the absorbent pad is fully within the U-shaped channel.

Protruding from the inside wall each linear member of the U, are a row of barbs, these barbs being slanted to permit sliding insertion of the pad from the distal end of the semi-rigid member to the seat defining the end of the U-shaped channel. Between the barbed sides of the U, the channel is partially open at the bottom of the U to expose the pad along its inserted elongate edge for both absorption of OMT during sample collection and to insure saturation of the pad once sample has been collected.

Insertion of the pad to the U-shaped channel section occurs by sliding the pad between the sides of the U until the pad comes into contact with the seat. At the same time, the barbs serve to retain the pad during collection of sample in the mouth between the cheek and gum and against the forces of centrifugation in the lab.

The vial is provided with an annulus adjacent to but spaced above its closed end. This annulus preferably comprises an odd number of flutes or chord like protrusion truncating the otherwise cylindrical interior of the bottom of the vial. The fluted construction enables the vial to accommodate the necessary volume of sample and preservative below the annulus. At the same time, the fluted construction does not require the length of the vial to be extended so as not to fit within swinging bucket type centrifuge rotors commonly used for preserved sample extraction.

In the event that the pad becomes detached from its channel in the semi-rigid holding member during centrifugation, the dimension of the vial is reduced by the annulus. This reduction in dimension is sufficient to physically interfere with the pads width dimension and to prevent the pad from moving into the space at the bottom of the vial and re-absorbing separated preserved sample if separation from the semi-rigid pad holding member occurs.

When shipped and before sample collection, the needed preservative is sealed by the closure member. At the same time, the pad on the semi-rigid pad holding member protrudes away from the vial. Preferably, both the semi-rigid pad holding member and absorbent pad are covered by a tubular cap—having similar dimension and being disposed on the opposite side of the closure member from the vial.

Once sample has been collected and the pad inserted into the interior of the vial, it is important that mixing of the preservative with the sample occur quickly. Accordingly, the outside of the closed end of the sample tube is rounded to prevent standing of the vial which could prevent absorption of the preservative to the pad.

At the bottom of the vial—adjacent the fluted portion of the vial, there is a volume adequacy line. This line provides a volumetric check to assure the presence of sample and preservative in sufficient quantity after centrifugation to indicate a valid sample collection.

In another aspect, the present invention provides a method for recovering and testing substances, comprising the steps of:

(a) inserting an absorbent member treated with a hypertonic solution and connected to a first end of a closure member into an area which contains the substances to be tested to recover a high concentration of the substances, a second end of the closure member being attached to a vial, containing a preservative, which provides a handle for inserting the absorbent member;

(b) removing the absorbent member from the area which contains the substances to be tested;

(c) removing the second end of the closure member from a first end of the vial containing the preservative;

(d) inserting the absorbent member into the vial; and (e) securing the first end of the closure member to the first end of the vial.

BRIEF DESCRIPTION OF THE DRAWINGS

The foregoing summary, as well as the following detailed description of a preferred embodiment of the invention, will be better understood when read in conjunction with the appended drawings. For the purpose of illustrating the invention, there is shown in the drawings an embodiment which is presently preferred. It should be understood, however, that the invention is not limited to the precise arrangements and instrumentalities shown. In the drawings.

DESCRIPTION OF THE PREFERRED EMBODIMENT

Figure 1:
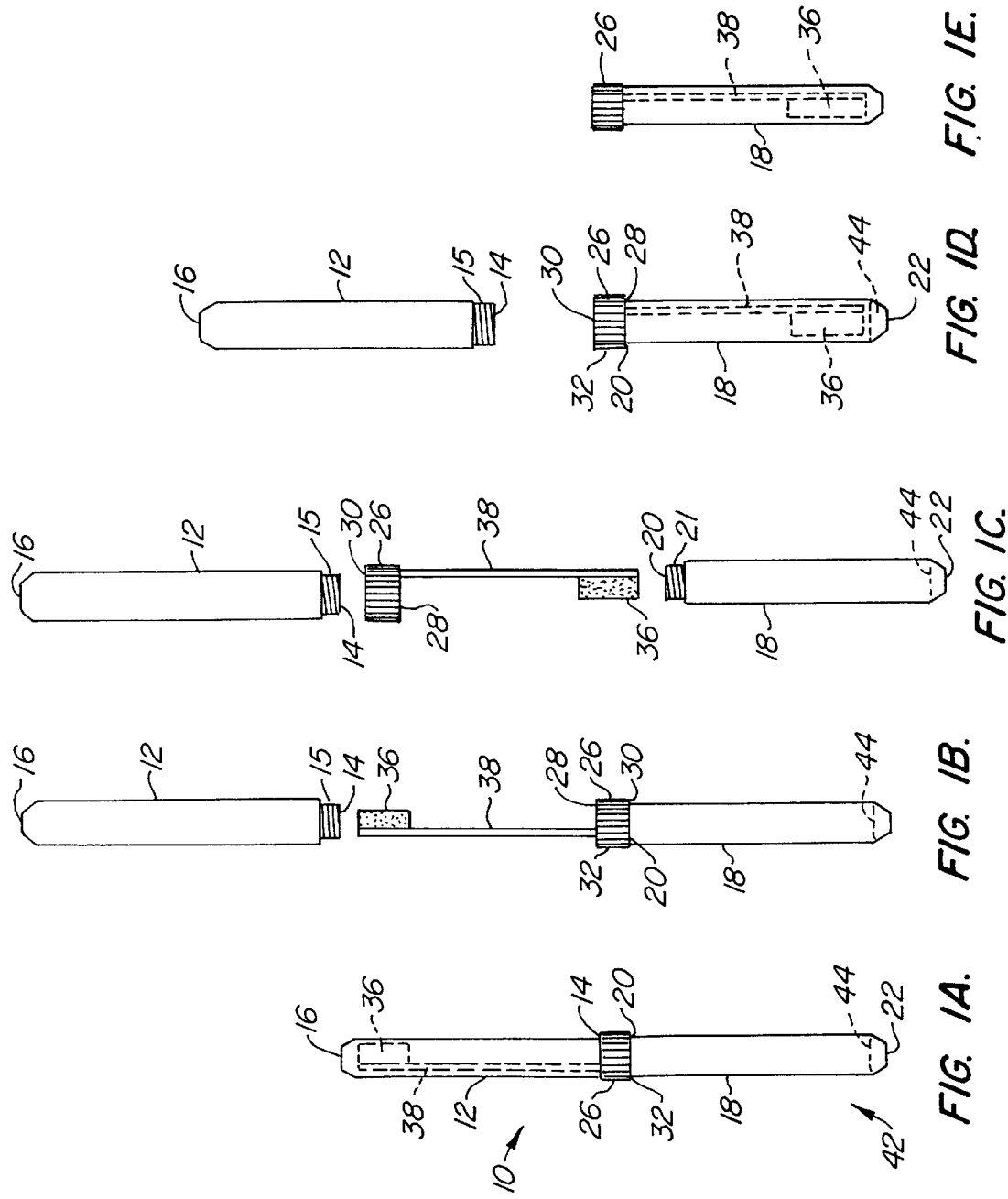
FIGS. 1(a)–(e) are a schematic flow diagram demonstrating the use of a collection device in accordance with a preferred embodiment of the present invention.

Certain terminology is used in the following description for convenience only and is not limiting. The words "right," "left," "lower" and "upper" designate directions in the drawings to which reference is made. The words "inwardly"

and "outwardly" refer to directions toward and away from, respectively, the geometric center of the substance collection and preserving device of the present invention and designated parts thereof. The terminology includes the words above specifically mentioned, derivatives thereof and words of similar import.

Referring to the drawings, wherein like numerals indicate like elements throughout, there is shown in FIGS. 1(a)–(e), 2 and 3 a preferred embodiment of collection device 10 for collecting and preserving substances.

As shown in FIGS. 1(a)–(e) and 2, collection device 10 comprises vial 18 having generally open end 20 and closed end 22. Open end 20 of vial 18 is adapted to be engaged and closed by removable closure member 26, described in more detail below.

In the preferred embodiment, collection device 10 further includes a cover 12 having open end 14 and closed end 16. Open end 14 is adapted to be engaged and closed by removable closure member 26. However, it will be recognized by those skilled in the art that the cover 12 is optional, and collection device 10 may be supplied in a sealed package or carton without cover 12.

In the preferred embodiment, cover 12 and vial 18 are generally cylindrical in shape with a generally uniform internal cross section and are interchangeable. In the preferred embodiment, vial 18 is adapted to fit into a centrifuge. However, it will be recognized by those skilled in the art that cover 12 and vial 18 may have different cross-sections, such as hexagonal or octagonal, or their external shapes may include different features, such as textured areas or flat spots for ease in opening and closing, or various markings to differentiate cover 12 and the vial 18 from each other. Preferably, open end 14, 20 of each of cover 12 and vial 18 is threaded with external threads 15, 21. Preferably, cover 12 and vial 18 are made of a suitable material which is impervious to the substances to be collected and tested. For collection devices 10 to be used for testing substances from a person's oral cavity, cover 12 and vial 18 are preferably made from polyethylene, polypropylene, polyvinyl chloride, glass, or another suitable polymeric material, by molding, or any other suitable process.

Collection device 10 further comprises removable closure member 26 which is generally cylindrically shaped and includes first closure end 28 and second closure end 30, at least one of which and preferably both of which are engageable with open end 20 of vial 18. Preferably, second closure end 30 of removable closure member 26 initially sealingly closes open end 20 of vial 18, as shown in FIGS. 1(a) and 1(b).

In the preferred embodiment, first closure end 28 and second closure end 30 of closure member 26 are also engageable with open end 14 of cover 12 with first closure end 28 of removable closure member 26 initially sealingly closing the first end 14 of cover 12, as shown in FIG. 1(a). As shown most clearly in FIG. 2, at least one and preferably both first closure end 28 and second closure end 30 of removable closure member 26 are threaded with substantially identical internal threads 29, 31 which complement external threads 15, 21 on open end 14 and open end 20 of cover 12 and vial 18, respectively.

Preferably, the external surface of the removable closure member 26 includes spaced serration 32. In the preferred embodiment, removable closure member 26 is made of a suitable material, such as polyethylene or polypropylene, and is preferably molded with external serration 32 and identical internal threads 29, 31. However, it will be recognized by those skilled in the art that other suitable polymeric materials may be used, and the external surface of the closure member can have various shapes and may be smooth, knurled or formed in some other manner. Additionally, flat annular gaskets 40 formed of an elastomeric material or any other suitable sealing material may be provided inside first closure end 28 and second closure end 30 of removable closure member 26 to ensure that the removable closure member sealingly closes at least open end 20 of vial 18.

While cover 12 and vial 18 include external threads 15 and external threads 21 respectively, closure member 26 includes identical internal threads 29 and identical internal threads 31, it will be recognized by those skilled in the art from the present disclosure that internal threads could be provided in cover 12 and vial 18, and removable closure member 26 could have external threads, or that other fastening means, such as a snap fit over or under an annular ring or a press fit or any other suitable method could be used to secure closure member 26 to vial 18 and cover 12.

Figure 2:
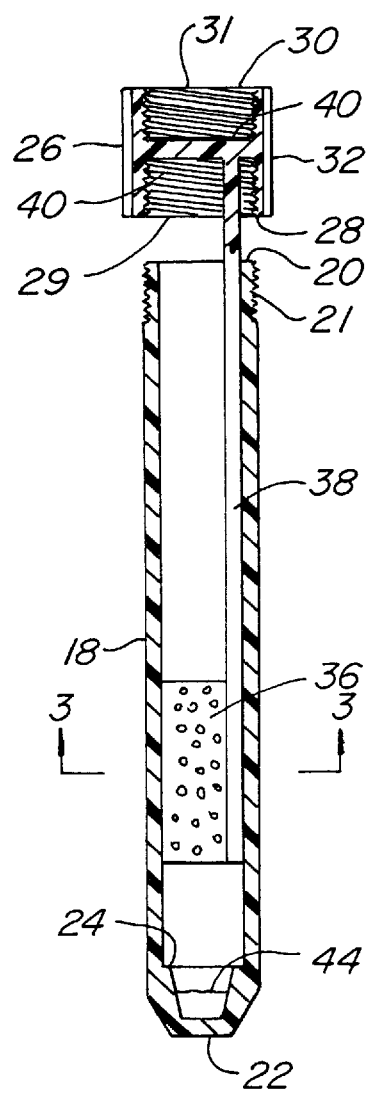
FIG. 2 is a longitudinal section of a portion of a collection device in accordance with a preferred embodiment of the present invention.

As shown in FIGS. 1(a)–(e), 2 and 3, absorbent member 36 is attached to the removable closure member 26. Absorbent member 36 may be loose, i.e., not attached, if desired. Absorbent member 36 is adapted to be received in vial 18, and also in cover 12. Preferably, absorbent member 36 is attached to first closure end 28 of closure member 26 by elongated semi-rigid stem 38 which can be formed as an integral part of the closure member 26. Alternatively, elongated semi-rigid stem 38 could be formed separately from closure member 36 and later attached. Elongated semi-rigid stem 38 is preferably a hollow plastic stick member having groove 39 at one end into which the absorbent member 36 is inserted. Elongated semi-rigid stem 38 has a length which is shorter than the length of vial 18, and holds absorbent member 36 at least a predetermined minimum distance above closed end 22 of vial 18. Preferably, absorbent member 36 is located outside vial 18 prior to use, with open end 20 of vial 18 being secured to second closure end 30 of closure member 26 to provide a handle, as shown in FIG. 1(b). In the preferred embodiment, absorbent member 36 is located inside cover 12 prior to use, as shown in FIG. 1(a), and first closure end 28 of removable closure member 26 is removed from open end 14 of cover 12 to uncover and expose absorbent member 36, as shown in FIG. 1(b). After use, second closure end 30 of closure member 26 is removed from open end 20, vial 18 is inverted, as shown in FIG. 1(c), and absorbent member 36 is then inserted into vial 18, as shown in FIG. 1(d) and FIG. 2. first closure end 28 of closure member 26 is then sealingly engaged to open end 20 of vial 18, as shown in FIG. 1(d). If desired, vial 18 may be engaged with second closure end 30 of removable closure member 26 as shown in FIG. 1(e) or may be discarded.

Figure 3:
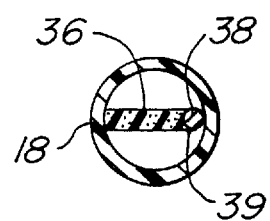
FIG. 3 is a section view taken along line 3—3 in FIG. 2.

In the preferred embodiment, absorbent member 36 is made of an absorbent material which can be effectively placed in the oral cavity. Preferably, a plastic or carbohydrate material such as cellulose can be used as the absorbent material, but a thick, absorbent cotton paper pad is preferred. An example of a thick, absorbent cotton paper is product no. 300 manufactured by Schleicher and Schuell in Keene, N.H. In the preferred embodiment, the width of absorbent member 36 is approximately the same as the internal diameter of vial 18, as shown in FIG. 3.

Referring now to FIG. 2, in the preferred embodiment, annular shoulder 24 is located in vial 18 a predetermined distance above closed end 22. Annular shoulder 24 functions alone if absorbent member 36 is not attached to closure member 26 or cooperates with elongated semi-rigid stem 38 to maintain or support absorbent member 36 a predetermined distance away from closed end 22 of vial 18, to prevent absorbent member 36 from being moved to a position below the predetermined distance from closed end 22 of vial 18, particularly if absorbent member 36 becomes separated from elongated semi-rigid stem 38 during further processing, as described in more detail below. Preferably, annular shoulder 24 is formed with vial 18 as vial 18 is manufactured. It will be recognized by those skilled in the art from this disclosure that other means may be used to support absorbent member 36, such as ribs extending upward from closed end 22 of vial 18, an annular ring, a tapered side wall adjacent to the bottom of vial 18, or the like. It will be similarly recognized that the support means need not be formed with vial 18, but may be added or formed in a secondary operation.

In the preferred embodiment, collection device 10 is provided as a kit 42 for collecting and storing substances for subsequent testing. Kit 42 comprises the collection device 10, as described above, wherein absorbent member 36 is initially treated with a hypertonic solution, such as that described in the U.S. Pat. No. 5,103,836, which is incorporated herein by reference as if fully set forth. In particular, a hypertonic solution is a salt solution which has an ionic strength exceeding that found in blood. Cover means, such as cover 12 or a separate package or carton, initially shields the absorbent member 36 prior to use to prevent contamination.

Preferably, preservative fluid 44, such as that described in U.S. Pat. No. 5,103,836, is located in vial 18, and second closure end 30 of closure member 26 is sealingly engaged with open end 20 of vial 18. Preferably, up to approximately two (2) ml of preservative fluid 44 is located in vial 18, such that when vial 18 is in the upright position, the level of preservative fluid 44 is below the predetermined distance from closed end 22 of vial 18, and if absorbent member 36 is inserted into the upright vial 18 it does not contact preservative fluid 44.

Kit 42 can be provided with breakaway seals on open end 14 and open end 20 of cover 12 and vial 18, or other tamper evident means, such as separate seals or tabs, to indicate whether the kit has been previously used or opened.

The present invention is suitable for use in recovering and testing substances, such as immunoglobulins in saliva or other such fluids, or other substances having molecular weights ranging from about 176 to about 950,000 as set forth in U.S. Pat. No. 5,103,836. A method for recovering and preserving substances will be described below in connection with FIG. 1(a)–(e).

If cover 12 is present, first closure end 28 of closure member 26 is removed from open end 14 of cover 12 to uncover and expose absorbent member 36, as shown in FIGS. 1(a)–(b). Absorbent member 36 is preferably previously treated with a hypertonic solution and is attached to closure member 26. Using vial 18 as a handle, absorbent member 36 is inserted into an area which contains the substances to be tested to recover a high concentration of the substances. In the preferred usage, absorbent member 36 is placed between the cheek and gum to facilitate absorption of secretions originating from the gingival lymphoid tissue, as well as secretions from the submucosal lymphoid tissue and salivary gland lymphoid tissue. It is preferable that the specimen of the substance be collected by rubbing absorbent member 36 back and forth between the gums and cheek for about ten (10) seconds and then holding absorbent member 36 in position for about two minutes.

Absorbent member 36 is thereafter removed from the area which contains the substances to be tested, and second closure end 30 of closure member 26 is removed from open end 20 of vial 18, keeping open end 20 of vial 18 facing upwardly to prevent loss of preservative fluid 44 within vial 18, as shown in FIGS. 1(b)–(c). Closure member 26 is inverted and absorbent member 36 is inserted into vial 18 and first closure end 28 of vial 18. Sealed vial 18 is then tilted from side to side or is otherwise manipulated such that preservative fluid 44 located at closed end 22 of vial 18 contacts and is absorbed by absorbent member 36. The preservative greatly improves the preservation of oral immunoglobulin when the preservative solution is used, as explained in detail in U.S. Pat. 5,103,836. If desired, open end 14 of cover 12 may be engaged with second closure end 30 of closure member 26.

There is no need to set down either closure member 26, with the attached absorbent member 36, or the vial 18 during the entire process of collecting a specimen of the substances to be tested which could result in spilling the preservative or contamination of the collected substances. The user of collection device 10 can always hold vial 18 and closure member 26 with attached absorbent member 36 in his or her hands throughout the procedure. But if the device must be put down either before or after sample collection, the design of the closure, vial, and stick is such that absorbent pad will not contact a generally flat surface, thereby avoiding contamination.

Once sealed vial 18 with the substances to be tested is sent to the lab, it can be inserted directly into a centrifuge, and the collected substances and preservative removed from absorbent material 36 by centrifugation. The collected substances and preservative are forced to closed end 22 of vial 12, and are located below the predetermined level, defined by annular shoulder 24. Annular shoulder 24 prevents absorbent member 36 from dropping into and re-absorbing the separated collected substances and preservative should absorbent member 36 become dislodged from elongated semi-rigid stem 38 as a result of centrifugation or other processing. Closure member 26 and attached semi-rigid stem and absorbent member is then removed and discarded without the need for separately handling absorbent member 36, or any intermediate steps or handling, of sealed vial 18, making the lab test less labor intensive which should result in a reduction in cost. This type of vial arrangement is also suitable for use with automated lab systems.

The collected substances are then generally removed from closed end 22 of vial 18 with a micropipette or other device or method (not shown) for testing.

Having given a general description, details of the construction of collection device 10 can now be set forth.

Figure 4:
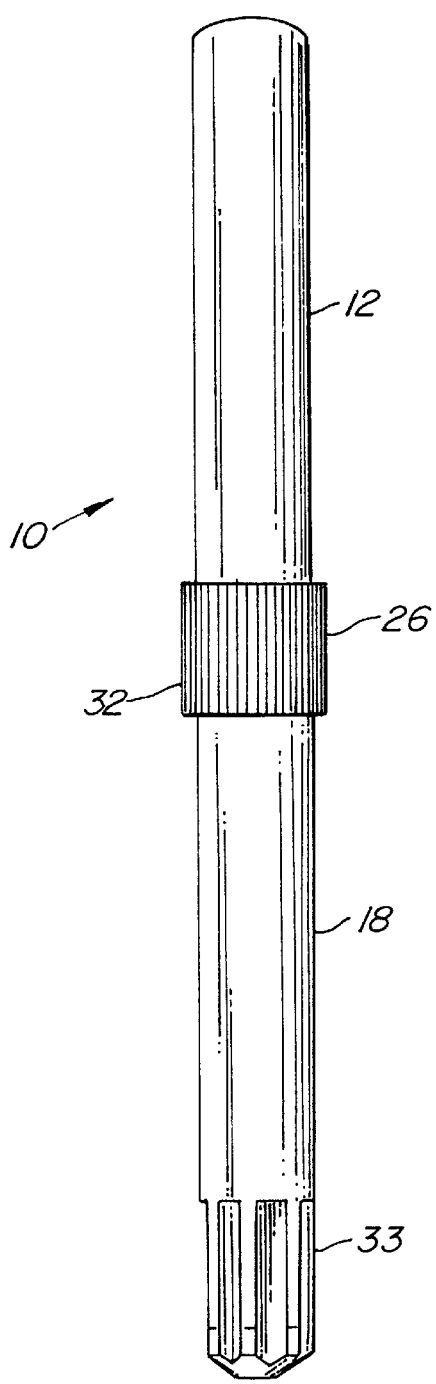
FIG. 4 is a side elevation of the vial, the closure member attached to the vial, and a cap mounted over the closure member and semi-rigid pad holding member and pad for enabling the collection device of this disclosure to be shipped for collection without moisture or other contamination of the pad.

Referring to FIG. 4, collection device 10 is illustrated having cover 12, vial 18, and removable closure member 26 connecting cover 12 and vial 18. Removable closure member 26 is provided with spaced serration 32; likewise, vial 18 is provided with exterior fluting 33. These respective spaced serration 32 and exterior fluting 33 enable removable closure member 26 to be readily separated from vial 18.

Figure 5A:
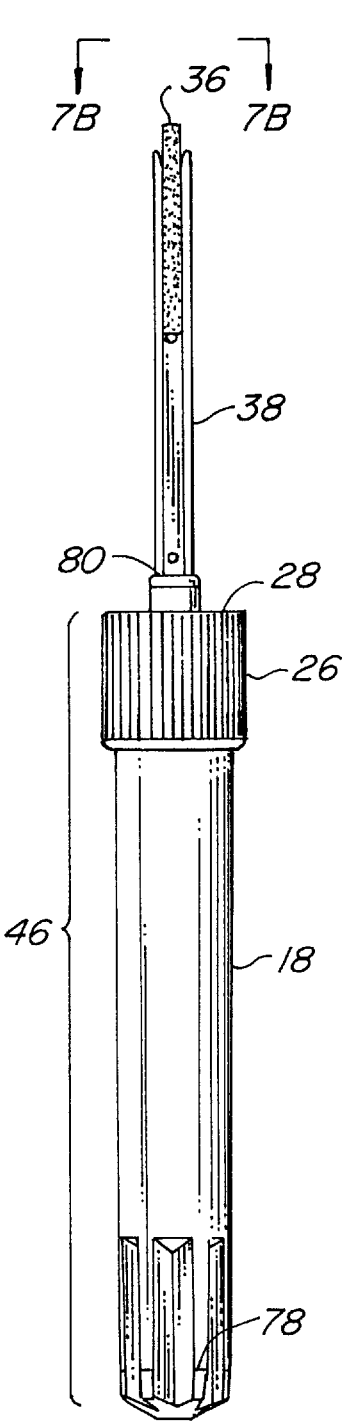
FIG. 5A is a view identical to FIG. 4 with the protecting cap removed and the absorbent collection pad exposed for collection.
Figure 5B:
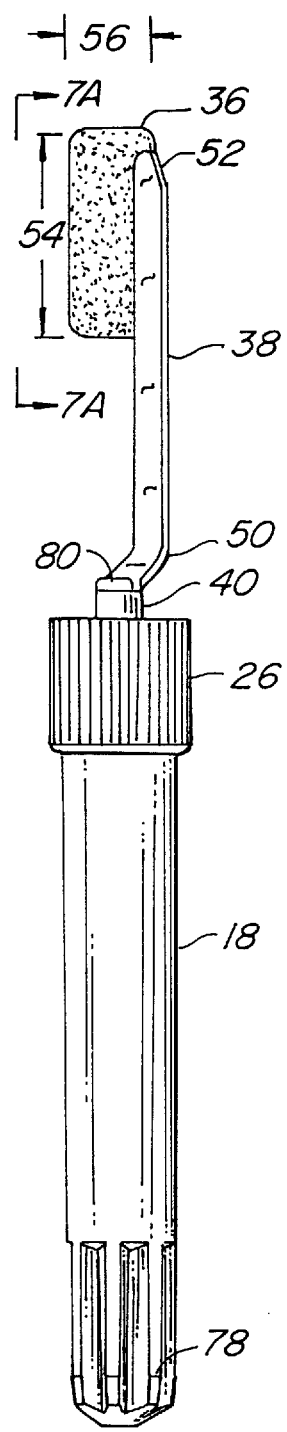
FIG. 5B is a side elevation similar to FIG. 5A taken along a major surface of the pad.
Figure 5C:
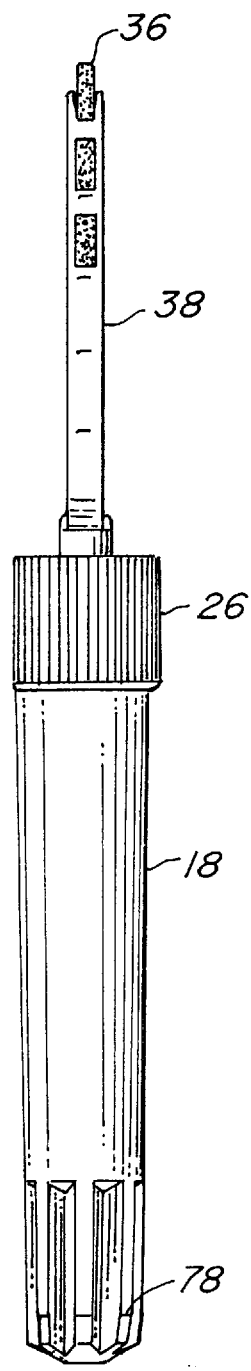
FIG. 5C is a side elevation illustrating the back of the semi-rigid pad holding member illustrating the openings in the back of the semi-rigid pad hold member for improving absorption by the pad.

Referring to FIGS. 5A–5B, cover 12 has been removed. This exposes elongated semi-rigid stem 38 and absorbent member 36. At this juncture, it is possible to understand that vial 18 and removable closure member 26 form a manipulative handle 46 for elongated semi-rigid stem 38 and absorbent member 36 during sample collection.

Some attention can now be given to the specific configuration of elongated semi-rigid stem 38. Elongated semi-rigid stem 38 mounts to chimney 48 protruding axially and centrally from first closure end 28. At chimney 48, elongated semi-rigid stem 38 angularly extends at crook 50 toward a side disposition parallel to both the interior side of removed cover 12 and vial 18. As will be made apparent, this disposition of elongated semi-rigid stem 38 enables absorbent member 36 to absorb preservative fluid 44 upon insertion of absorbent member 36 to vial 18. From crook 50, elongated semi-rigid stem 38 extends upward to distal end 52.

Figure 7B:
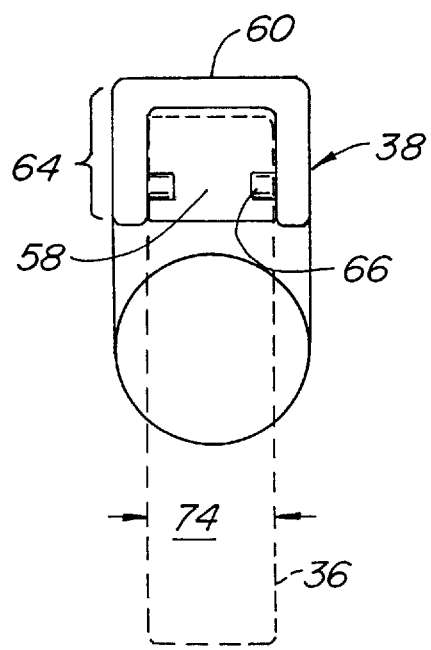
Figure 7A:
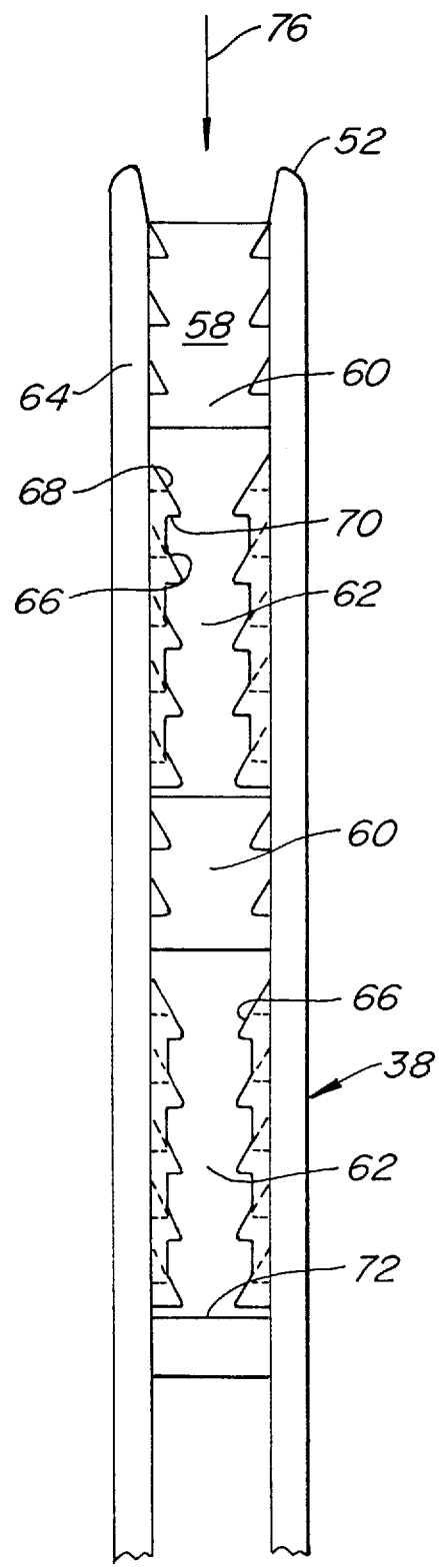

Absorbent member 36 is a rectilinear pad. This rectilinear pad has elongate length 54 and width 56. Width 56 is selected so that absorbent member 36 and elongated semi-rigid stem 38 fit to vial 18 with minimum clearance. Turning to the details of FIGS. 7A and 7B, fitting of absorbent member 36 along elongate length 54 to distal end 52 of elongated semi-rigid stem 38 can be understood.

Referring to FIG. 7, it will be understood that elongated semi-rigid stem 38 defines U-shaped channel 58. U-shaped channel 58 has intermittent bridges 60 connecting the respective sides of the U with open channel windows 62 there between. Along the inside edge of linear side members 64 of the U, there are placed barbs 66. Barbs 66 have inclined surfaces 68 facing towards distal end 52 of elongated semi-rigid stem 38 and retaining surfaces 70 facing away from distal end 52. Limiting the bottom of U-shaped channel 58 there is seat 72; this surface prevents absorbent member 36 from moving down the length of elongated semi-rigid stem 38 beyond seat 72.

Insertion of absorbent member 36 to U-shaped channel 58 is easily understood. Absorbent member 36 has thickness 74 slightly exceeding the inside dimension between linear side members 64. Absorbent member 36 is placed at one elongate length 54 into U-shaped channel 58 adjacent distal end 52. It is then slid downward in the direction of arrow 76. Barbs 66 scour into the surface of absorbent member 36, holding the member firmly on the end of elongated semi-rigid stem 38. It has been found that this particular fastening is highly advantageous. It does not use adhesives—which might contaminate the sensitive testing of the sample. Further, the grip on absorbent member 36 is sufficient so that in most cases the full forces of centrifugation necessary to remove sample for absorbent member can be resisted.

Understanding the assembly of absorbent member 36 to elongated semi-rigid stem 38, the remainder of the detailed description can be understood. Specifically, vial 18 when shipped for sample collection contains up to 2 milliliters of preservative fluid 44. At the same time, when sample is taken and extracted from absorbent member 36 by centrifugation, the total sample and preservative will exceed the original volume of preservative. This being the case, vial 18 is provided with volume adequacy line 78. If the preservative and sample when extracted from absorbent member 36 by centrifugation do not approach this line, it is known that defective sample collection has occurred; consequently, analysis of the sample is aborted.

Finally, elongated semi-rigid stem 38 adjacent chimney 48 is provided with compression seat 80. Compression seat 80 enables automated placement of elongated semi-rigid stem 38 in chimney 48.

Figure 6A:
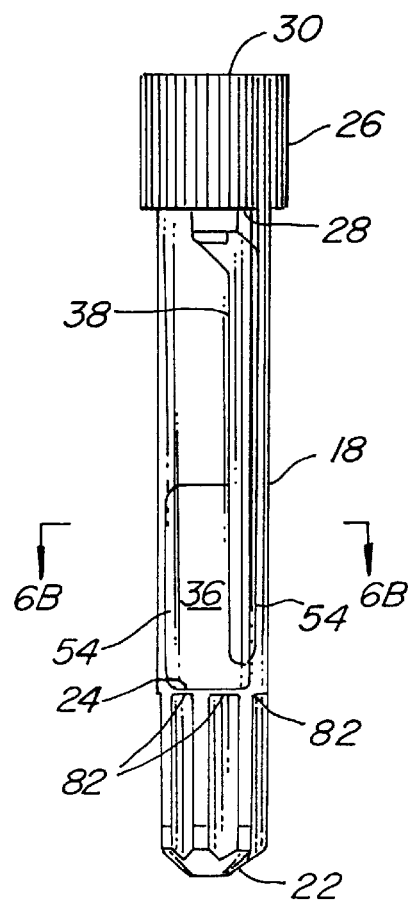
FIG. 6A is a side elevation of the collection device after sample collection with the semi-rigid pad holding member inserted into the vial, and specifically illustrating how the semi-rigid member holds the elongate inside of the rectilinear pad adjacent the sides of the vial.

Referring to FIG. 6A, vial 18 is shown with removable closure member 26 inverted and first closure end 28 attached to the vial. In this disposition, it can be seen that crook 50 disposes elongated semi-rigid stem 38 along side wall of vial 18. This disposes absorbent member 36 at elongate lengths 54 immediately adjacent the inside sidewalls of vial 18. With this disposition, absorbent member 36 is readily saturated with preservative fluid 44 (See FIG. 2), once sample has been taken to absorbent member 36 and vial 18 has been properly manipulated to assure pad-preservative contact.

Figure 6B:
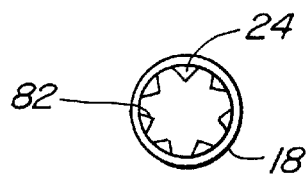
FIG. 6B is a section taken along lines 6B—6B of FIG. 6A illustrating the fluting at the bottom of the vial; and, FIG. 7A and 7B are enlarged details of the end of the pad holding semi-rigid member illustrating in detail the pad holding barbs enabling insertion of the pad and retention of the pad during collection and centrifugation, these views being taken along lines 7A—7A of FIG. 5B and lines 7B—7B of FIG. 5A, respectively.

Referring further to FIGS. 6A and 6B adjacent closed end 22 of vial 18, it will be seen that V-shaped flutes 82 are located on the inside of the vial. These flutes—preferably an odd number of flutes (here 7 flutes)—define annular shoulders 24 immediately below absorbent member 36. This construction has the advantage of preventing absorbent member 36 from falling to the bottom of vial 18 and absorbing sample and preservative after centrifugation. At the same time, flutes 82 do not appreciably interfere with the volumetric capacity of vial 18 requiring an elongation of the vial that might otherwise interfere with the use of conventional swinging bucket rotors for centrifugation.

It has been found that if absorbent member 36 become detached before appreciable quantities of sample and preservative are removed, annular shoulder 24 prevents absorbent member 36 from moving and reabsorbing sample and preservative. Further, and where absorbent member 36 become loose when most of the sample and preservative has been removed, rectilinear absorbent member 36 forms a canted disposition where it is partially held within U-shaped channel 58. In this canted disposition, it still interferes with annular shoulder 24 and therefore does not reabsorb centrifuged sample and preservative.

It will be understood that flutes 82 are a particularly advantageous construction; they enable sufficient volumes of sample and preservative to be retained without unduly elongating vial 18 so that it does not fit conventional swinging bucket centrifuges utilized in sample and preservative removal.

In order to further insure proper sequential removal of cover 12 and vial 18, these respective components can be assembled to removable closure member 26 with differential fastening. Specifically, by using a relatively strong torque to assemble vial 18 to removable closure member 26 at identical internal threads 29 and weaker torque to assemble cover 12 to removable closure member 26 at identical internal threads 31, separation in sequence will naturally occur. First, cover 12 will separate from removable closure member 26; second, vial 18 will separate from removable closure member 26.

It will be appreciated by those skilled in the art that changes could be made to the embodiment described above without departing from the broad inventive concept thereof. It is understood, therefore, that this invention is not limited to the particular embodiment disclosed, but it is intended to cover modifications within the spirit and scope of the present invention as defined by the appended claims.

What is claimed is:

1. A device for collecting substances comprising:
    a vial having a first open end, for being closed by a removable closure member, and a second closed end;
    a removable closure member having first end and second end which are each engageable with the first open end of the vial;
    an absorbent member attached to the removable closure member and is receivable in the vial whereby the absorbent member is located outside of the vial prior to use, with the first open end of the vial being secured to the second end of the closure member to provide a handle, and after use, the second end of the closure member is removed from the first open end of the vial, the closure member is inverted, the absorbent member is inserted in the vial and the first end of the closure member is removably engaged with the first open end of the vial, the absorbent member having an absorption volume sufficient to receive adequate sample for testing;

a known volume of preservative fluid is located in the vial;

a volume adequacy line configured on the vial to define a volume within the vial for containing the known volume of preservative fluid and adequate sample from the absorbent member for testing.

2. The collection device of claim 1 wherein said vial is adapted to fit into a centrifuge.

3. The collection device of claim 1 further comprising:

a cover having a first, generally open end, for being closed by the removable closure member, and a second, generally closed end, the first end of the closure member being engageable with the first end of the cover, whereby the absorbent member is located inside the cover prior to use, with the first end of the closure member being removably engaged to the first end of the cover, and the cover is removed from the first end of the closure member to uncover and expose the absorbent member.

4. The collection device of claim 3 wherein the first end of each of the vial and the cover is threaded with an external thread and the first and second ends of the closure member are threaded with internal threads which complement the threads of the vial and the cover.

5. The collection device of claim 1 wherein the absorbent member is attached to the first end of the closure member by a stem.

6. The collection device of claim 1 wherein when the absorbent member is inserted into the vial, the absorbent member is held a predetermined distance away from the second end of the vial.

7. The collection device of claim 6 further comprising support means located in the vial for supporting the absorbent member the predetermined distance from the second end of the vial.

8. The collection device of claim 6 wherein a stem holds the absorbent member the predetermined distance from the second end of the vial.

9. A kit for collecting and storing substances for subsequent testing comprising the collection device of claim 1 wherein the absorbent member is treated with a salt solution which has an ionic strength exceeding that found in blood, cover means shield the absorbent member, and the second end of the closure member is engaged with the first end of the vial.

10. A method for recovering and testing substances, comprising the steps of:

providing a vial containing a known volume of preservative;

inserting an absorbent member connected to a first end of a closure member, the absorbent member treated with salt which generates a salt solution which has an ionic strength exceeding that found in blood when in an area which contains the substances to be tested, the absorbent member connected to a first end of a closure member to recover an adequate volume of the substances for testing, a second end of the closure member being attached to a vial containing the known volume of preservative which provides a handle for inserting the absorbent member;

removing the absorbent member from the area which contains the substances to be tested;

removing the second end of the closure member from the first end of the vial containing the preservative;

inserting the absorbent member into the vial; securing the first end of the closure member to the first end of the vial;

removing the substances to be tested from the absorbent member to the vial;

providing a volume adequacy line on the vial for indicating the presence of the known volume of preservative and the adequate volume of substances to be tested in the vial;

removing the substances to be tested and preservative from the absorbent member to the vial; and, observing the volume adequacy line to determine the presence of preservative and an adequate volume of substances to be tested.

11. The method of claim 10 further comprising the step of removing a cover from the first end of the closure member to uncover the absorbent member.

12. The method of claim 10 wherein the area which contains the substances to be tested is an oral cavity and the absorbent member is inserted into the oral cavity.

13. A device for collecting substances comprising:

an absorbent member for receiving a sample in a sufficient volume for testing;

a vial having a first open end for receiving the absorbent member and a second closed end;

preservative for preserving sample on the absorbent member; a restricted portion defined interior of the vial adjacent the second closed end having a dimension for excluding penetration of the absorbent member and having a volume sufficient to receive separated sample and preservative from the absorbent member;

means for sealing the vial at the first open end;

the vial is transparent; and, the restricted portion contains a volume so that when sufficient sample and preservative are resident in the restricted portion sufficient for testing the sample and preservative are held away from the absorbent member.

14. A device for collecting substances according to claim 13 and wherein:

the vial is a centrifuge sample tube.

15. A device for collecting substances according to claim 13 and wherein:

the restricted portion defined interiorly of the vial includes a circular section interrupted by chords.

16. A device for collection substances according to claim 13 and wherein:

the vial is transparent; and, the restricted portion contains a volume adequacy line to delimit when sufficient sample and preservative are resident in the restricted portion to indicate that sample is present in the preservative.

17. A device for collecting substances according to claim 13 and further comprising:

a rectilinear absorbent member having an length for being received into the vial and a width less than the first open end to permit the absorbent member to be received into the open end and a width greater than the restricted portion to prevent the absorbent member from penetrating the volume defined by the restricted portion interior of the vial.

18. A device for collecting substances comprising:

an absorbent member for receiving a sample;

a vial having a first open end for receiving the absorbent member and a second closed end;

preservative for preserving sample on the absorbent member;

means for sealing the vial at the first open end;

a handle for attachment to means for sealing at one end and to the absorbent member at the other end having a dimension for being received into the vial when the means for sealing seals the vial; and, the handle having a length to maintain the absorbent member away from the closed end of the vial a sufficient distance so that sample and preservative can collect at the bottom of the vial;

a restricted portion defined at the closed end of the vial having sufficient volume to receive sample and preservative separated from the absorbent member.

19. A device for collecting substances according to claim 18 and further including:

a restricted portion define at the closed end of the vial having sufficient volume to receive sample and preservative separated from the absorbent member; and, the handle having a length to maintain the absorbent member away from the restricted portion of vial.

20. A device for collecting substance according to claim 18 and wherein:

the vial is transparent; and, the second closed end of the vial has a volume adequacy line defining a volume within the vial for indicating the presence of sample and preservative.

21. A device for collecting substances comprising:

an absorbent member for receiving a sample, the absorbent member having at least one linear side and a predetermined thickness at the linear edge for being received into a handle;

a vial having a first open end for receiving the absorbent member and a second closed end;

preservative for preserving sample on the absorbent member;

means for sealing the vial at the first open end;

a handle for attachment to means for sealing at one end and to the absorbent member at the other end having a dimension for being received into the vial when the means for sealing seals the vial; and, a channel defined in the handle having pad retaining barbs, the pad retaining barbs for receiving the absorbent member at the at least one linear side with the pad retaining barbs permitting sliding insert of the absorbent member into the channel in a direction toward the means for sealing and for retaining the absorbent member against forces acting to move the absorbent member away from the means for sealing.

22. A device for collecting substances according to claim 21 and wherein:

the handle as attached to the means for sealing extends from the means for seal at a disposition to be immediately adjacent the side vial.

23. A device for collecting substances according to claim 21 and wherein:

the handle adjacent the channel is open to receive preservative to the absorbent member at the linear side.

24. A method of collecting substances for analysis comprising the steps of:

providing a sample vial defining an open end, and a closed end;

inserting sample preservative in the vial;

providing a vial closure having first and second ends for both sealing the vial;

attaching an absorbent pad to the first end of the vial closure;

sealing the vial with the second end of the vial closure to enable the vial to be used as a handle for sample collection and to permit the absorbent pad to protrude from the vial closure for sample collection;

collecting sample by holding the vial and manipulating the absorbent pad;

unsealing the vial at the second end of the vial closure; inserting the absorbent pad interior of the vial and resealing the vial and the first end of the vial closure;

shaking the re-sealed vial to saturate the absorbent pad with preservative;

placing the vial in a centrifuge and centrifuging the absorbent pad in the vial to remove the sample and preservative from the absorbent pad; and, analyzing the sample;

providing a transparent vial;

providing at the bottom of the transparent vial a volume adequacy line for determining the presence of sufficient volume of preservative and sample to indicate that sample has been taken;

after centrifuging the sample and preservative from the absorbent pad comparing the separated sample and preservative to the volume adequacy line to determine if sample has been taken; and, only after the comparing step indicates that sample has been taken, analyzing the sample.

* * * * *